(12) United States Patent
Liu

(10) Patent No.: US 12,178,568 B2
(45) Date of Patent: Dec. 31, 2024

(54) SAMPLING FACE MASK

(71) Applicant: Chia-Pin Liu, Taipei (TW)

(72) Inventor: Chia-Pin Liu, Taipei (TW)

( * ) Notice: Subject to any disclaimer, the term of this patent is extended or adjusted under 35 U.S.C. 154(b) by 471 days.

(21) Appl. No.: 17/380,031

(22) Filed: Jul. 20, 2021

(65) Prior Publication Data

US 2022/0031192 A1  Feb. 3, 2022

(30) Foreign Application Priority Data

Aug. 3, 2020 (TW) ................. 109126230

(51) Int. Cl.
*A61B 5/097* (2006.01)
*A61B 5/00* (2006.01)

(52) U.S. Cl.
CPC ............ *A61B 5/097* (2013.01); *A61B 5/6803* (2013.01); *A61B 2560/0443* (2013.01)

(58) Field of Classification Search
CPC .................. A61B 5/097; A61B 5/6803; A61B 2560/0443; A61B 2010/0087; A61B 10/0051; A61B 5/082; A61B 10/0096; A62B 18/02; A62B 18/08; A62B 23/02
See application file for complete search history.

(56) References Cited

U.S. PATENT DOCUMENTS

| | | | | |
|---|---|---|---|---|
| 11,020,619 B2* | 6/2021 | Castiglione | ............ | A62B 18/10 |
| 2010/0087749 A1* | 4/2010 | Tovey | ................. | A61B 5/097 |
| | | | | 600/543 |
| 2014/0216474 A1* | 8/2014 | Mittelstadt | ............ | A62B 27/00 |
| | | | | 128/863 |
| 2014/0251327 A1* | 9/2014 | Mittelstadt | ............ | A62B 27/00 |
| | | | | 128/205.24 |
| 2014/0373846 A1* | 12/2014 | Kao | ................. | A62B 18/006 |
| | | | | 128/205.12 |
| 2018/0125374 A1* | 5/2018 | Hall | ................. | A61B 5/082 |
| 2021/0325279 A1* | 10/2021 | Daniels | ............. | A61B 5/097 |
| 2022/0125333 A1* | 4/2022 | Alburty | ............. | A61B 5/097 |
| 2022/0192537 A1* | 6/2022 | Milner | ............. | G06N 20/00 |
| 2023/0200678 A1* | 6/2023 | Daniels | ............. | A61B 10/0045 |
| | | | | 600/532 |
| 2023/0263425 A1* | 8/2023 | Meirav | ............. | A61B 5/082 |
| | | | | 600/532 |
| 2024/0197202 A1* | 6/2024 | Andrasko | ............. | A61B 5/082 |

\* cited by examiner

*Primary Examiner* — Etsub D Berhanu
*Assistant Examiner* — Destiny J Cruickshank
(74) *Attorney, Agent, or Firm* — NZ CARR LAW OFFICE

(57) ABSTRACT

Disclosed herein is a sampling face mask. The sampling mask includes a mask body having a front side, a bottom, and one or more clamping blocks disposed on the bottom; a removable cartridge comprising a cartridge body having a chamber for housing the substances exhaled from the nose of the subject, and a door disposed above the chamber for opening or closing the chamber, and a driving means for driving the door to move laterally or vertically with respective to the cartridge body; wherein, the one or more clamping blocks can hold the door in place thereby keeping the door from closing; and when the one or more clamping blocks does not hold the door in place, the door is driven close via the driving means thereby closing the chamber and allowing the removable cartridge to be separated from the mask body.

10 Claims, 11 Drawing Sheets

SAMPLING FACE MASK

CROSS-REFERENCES TO RELATED APPLICATIONS

This application claims priority and the benefit of Taiwan Patent Application No. 109126230, filed Aug. 3, 2020, the entireties of which is incorporated herein by reference.

BACKGROUND OF THE INVENTION

1. Field of the Invention

The present disclosure relates to a sampling device. More particularly, the disclosure invention relates to a sampling face mask, which includes a removable cartridge capable of automatically closing after sampling or collecting exhaled substances of a subject.

2. Description of Related Art

Various types of masks for sampling the exhaled substances of a subject have been taught, for example, U.S. Pat. No. 5,474,060 describes a 3-dimensional (3-D) mask suitable for use in the sampling of substances exhaled from an individual. This 3-D mask includes removable hoses extended from inside of the mask for transporting the exhaled substances to an external device for subsequent identification. WO 2016/007749 discloses an oxygen mask, which includes a sampling port disposed on one side of the mask and coupled to an external container for collecting substances exhaled by its user. US 2010/0087749 teaches a cup-type mask or cornicle mask having components for collecting exhaled substances of a user. US 2018/0125374 teaches an exhaled gas analyzer, which also includes a mask having components (e.g., valves for directing the flow of gases) for collecting exhaled gases of a user. However, all the masks or analyzer described in the prior publication share a common disadvantage, that is, the risk of being cross-contaminated by its surrounding environment or by the process in which handling the sampling device with hand(s) or additional tools.

Accordingly, there exists in the related art a need of an improved sampling mask, in which the risk of cross-contamination is reduced to a minimal.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The first aspect of the present disclosure aims at providing a sampling face mask, which includes at least,
- a mask body having a front side substantially conforming to the shape of the nose of the subject, a bottom, and one or more clamping blocks disposed on the bottom;
- a removable cartridge removably coupled to the mask body comprising,
  - a cartridge body having a chamber for housing the substances exhaled from the nose of the subject; and
  - a door disposed above the chamber for opening or closing the chamber; and
- a driving means operably coupled to the mask body, the cartridge body, and the door for driving the door to move laterally or vertically with respect to the cartridge body;

wherein,
- the one or more clamping blocks of the mask body can hold the door in place thereby keeping the door from closing and the chamber being disposed substantially underneath the nose and stayed open; and
- when the one or more clamping blocks does not hold the door in place, the door is driven close via the driving means thereby closing the chamber and allowing the removable cartridge to be separated from the mask body.

According to embodiments of the present disclosure, the mask body has one or more breathable areas respectively disposed at positions corresponding a to both sides of the nose.

According to optional embodiments of the present disclosure, the sampling mask further comprises a base coupling to the bottom of the mask body for receiving the removable cartridge thereon.

According to embodiments of the present disclosure, the chamber is compartmented into one or more compartments.

According to optional embodiments of the present disclosure, the cartridge body further comprises one or more conduits independently coupled to the chamber or the one or more compartments.

According to embodiments of the present disclosure, the chamber is filled with or coated with a carrier for carrying the exhaled substances. Examples of the carrier suitable for use in the present disclosure include, but are not limited to, active carbon, alumina, carbon molecular sieve, polyacrylamide, silicone, zeolite, aminobenzyl methylcellulose, aminophenylene sulfide cellulose, diethylamine ethylcellulose, nitrobenzyl methylcellulose, nitrocellulose, and polyvinylidene fluoride.

According to embodiments of the present disclosure, the driving means may consist of one or more of a spring, a magnet, a rubber band, a rail, a guiding member, or a combination thereof. In some embodiments, the driving means is the combination of rails and springs. In other embodiments, the driving means is the combination of rails and magnets. In further embodiments, the driving means is the combination of rails and guiding members.

According to embodiments of the present disclosure, the door of the removable cartridge consists of one or more pieces of planks, and is driven to move laterally or vertically with respect to the cartridge body via the driving means.

According to embodiments of the present disclosure, the door is made of transparent, translucent, or opaque material.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1A:
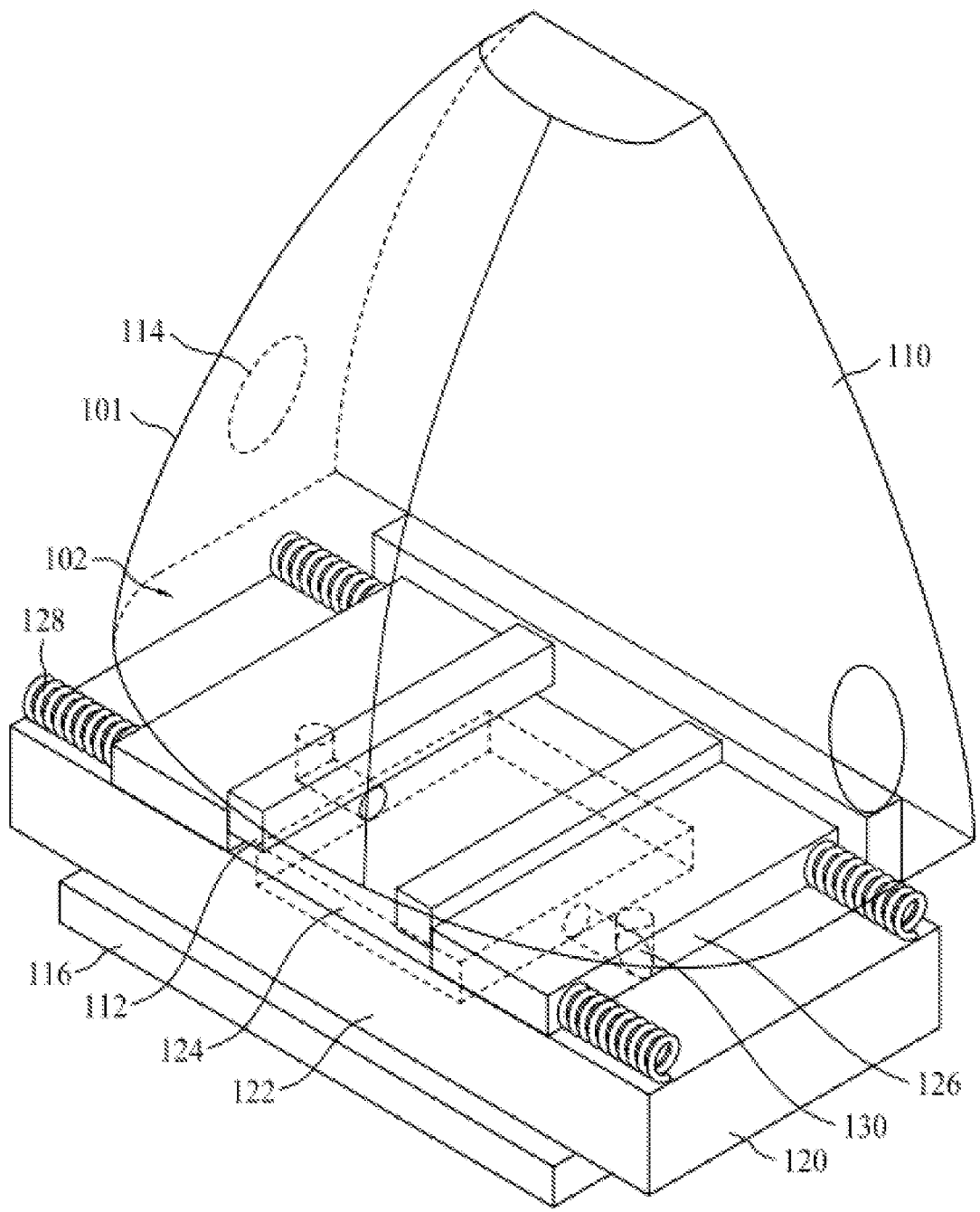
FIG. 1A is a schematic diagram depicting the sampling mask 100 in accordance with one embodiment of the present disclosure.

In accordance with common practice, the various described features/elements are not drawn to scale but instead are drawn to best illustrate specific features/elements relevant to the present invention.

Also, like reference numerals and designations in the various drawings are used to indicate like elements/parts.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless defined otherwise, all technical and scientific terms used herein have the same meaning as commonly understood by one of the ordinary skilled in the art to which this invention belongs. The singular forms "a", "and", and "the" are used herein to include plural referents unless the context clearly dictates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "subject" and "individual" may be used interchangeably throughout the present disclosure, and refers to someone whose exhaled substances are collected or harvested by the sampling mask described herein. The term "subject" is intended to refer to both the male and female gender unless one gender is specifically indicated. Examples of the subject include, but are not limited to, a human, a mouse, a rat, a hamster, a guinea pig, a rabbit, a dog, a cat, a cow, a goat, a sheep, a monkey, and a horse. According to preferred embodiments, the subject is a human.

The term "mask" as used herein refers to a 3-dimensional cover overlying at least the nose and/or its neighboring area of the face of an individual.

The term "exhaled substances" refers to substances exhaled from the respiratory system of an individual, in which the substance may be in the form of a gas (e.g., a gas composed of one single volatile compound or a mixture of volatile organic compounds), a liquid or a solid. Exemplary exhaled substances include, but are not limited to, foreign substances and/or microorganisms exhaled from the lungs of an individual; substances secreted from the nose or respiratory system of an individual; tissues, cells, nucleic acids and/or metabolites detached from the respiratory system of an individual.

The term "carry or carrying" refers to actions that collect or harvest the exhaled substances from the nose or respiratory system of an individual. The action may take the form of adsorbing or capturing molecules, and may involve affinity or non-affinity binding between two molecules, or physical or chemical binding between two molecules.

The term "breathable material" as used herein refers to a material in which small molecules such as air (e.g., exhaled gas) and moisture may pass freely.

II. The Present Sampling Face Mask

The present disclosure aims at providing an improved face mask for sampling exhaled substances from an individual without the risk of being contaminated by the surrounding environment or even by the process in which handling the sampling device with hand(s) or additional tools. Further, present practice for sampling exhaled substances from an individual, in general, requires at least two persons working together for the task, accordingly, it will also put the two persons at risk of being contaminated during sampling. Thus, the present disclosure aims at providing an improved sampling face mask that addresses the contamination issue described above, in which the exhaled substances from the sampling subject are collected and housed in a closed chamber, thereby reducing the possibility of the harvested exhaled substances being contaminated by their surrounding environment or by the process dealing with handling the sampling device with hand(s) or additional tools.

Figure 1B:
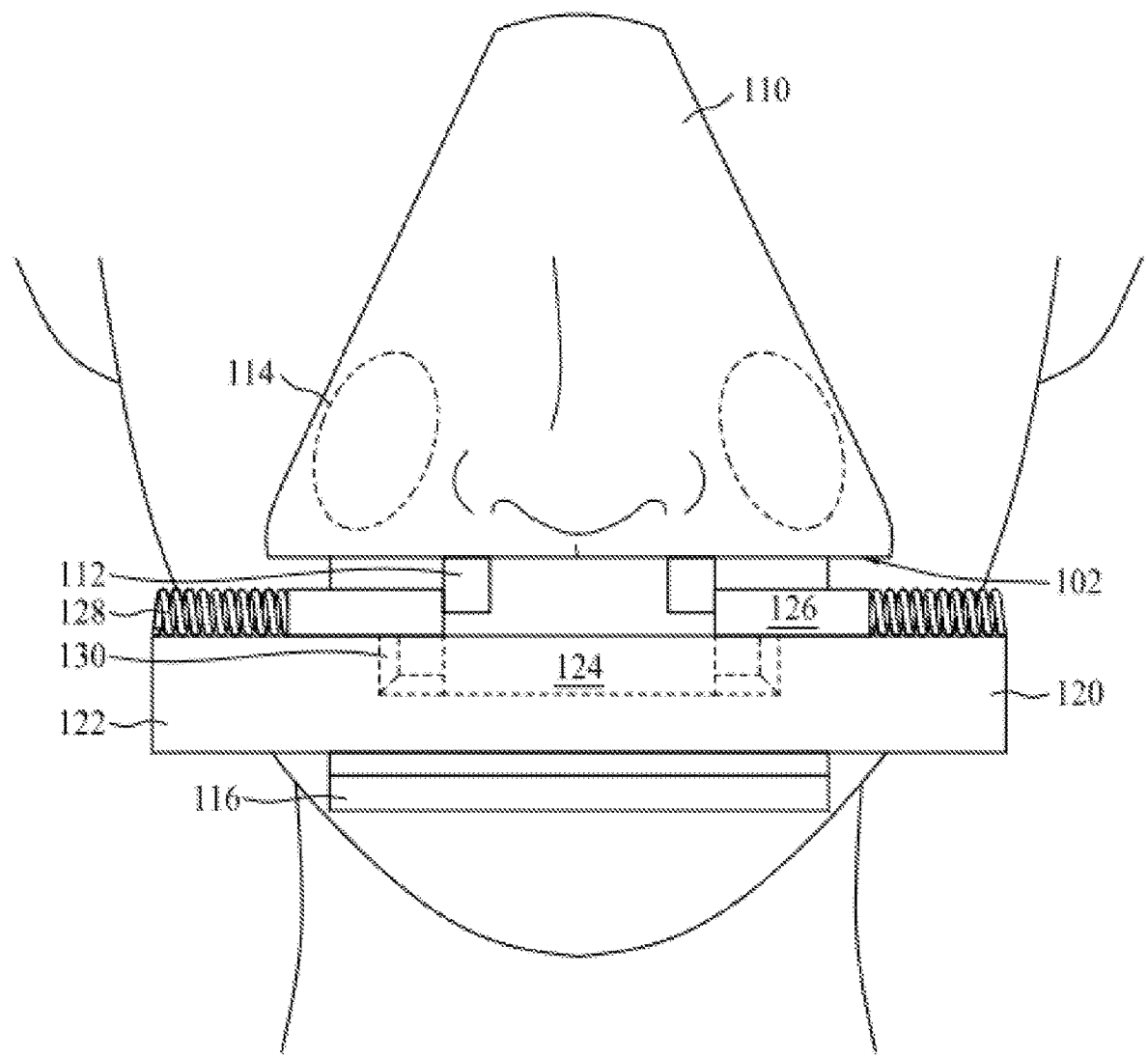
FIG. 1B is schematic diagram depicting a user wearing the sampling mask 100 of FIG. 1A.

Referring to FIGS. 1A to 1D, which depict the first embodiment of the present sampling face mask 100. FIG. 1A is a representative schematic drawing depicting the layout of the sampling face mask 100, and FIG. 1B is a representative schematic drawing depicting the sampling face mask 100 of FIG. 1A in use. The sampling face mask 100 includes in its structure at least, a mask body 110; and a removable cartridge 120 removably coupled to the mask body 110. The mask body 110 has a front side 101, a bottom 102, and one or more clamping blocks 112 disposed on the bottom 102, in which the front side 101 has a size that substantially covers the nose of a subject; preferably, it is conformed to the shape of the nose (See FIG. 1B). Alternatively or optionally, the sampling mask 100 further includes a base 116 removably coupled to the bottom of the mask body 110 for supporting the removable cartridge 120 thereon. When in use (i.e., when a subject puts the mask body 110 on his/her face and covers the nose), the removable cartridge 120 would be at the position close to the two nostrils for easy collection of any substances exhaled from the nose of the subject. The mask body 110, in general, is made of a material that is breathable and/or filterable (e.g., the material suitable for the manufacture of surgical masks, N95 masks, or N99 masks). Alternatively, the mask body 110 is made of a material that is not breathable. Preferably, the mask body 110 is made of both materials (i.e., non-breathable material and breathable material), in which the part of the mask body 110 made of the breathable material forms a breathable area that prevents pressure (i.e., pressure resulted from the exhaled gas accumulated overtime in the mask body) from building up in the mask body 110. In the case when the built-up pressure becomes too high, the exhaled gas accumulated in the mask body 110 might leak from any gaps present between the mask body 110 and the nose. Note that the exhaled gas that leaks out of the face mask 100 might contaminate its surrounding environment and/or personnel. Preferably, the mask body 110 includes one or more breathable areas 114 independently disposed on the front side of the mask body corresponding to the left or right sides of the nose to facilitate diffusion of air and normal breathing of the subject. According to optional embodiments of the present disclosure, the mask body 110 may further include one or more filters (not depicted) independently disposed at positions above the one or more breathable areas 114. The one or more filters independently comprises a membrane for filtering air. Alternatively, or optionally, the one or more filters may further include one or more one-way valves (not depicted) disposed at one or two sides of the membrane for directing the flow of the air. According to one optional embodiment of the present disclosure, the one or more filters further include one or more one-way valves (not depicted) disposed at positions above the one or more breathable areas 114 for detecting the air flow (e.g., for detecting the presence of any exhaled gas).

The mask body 110 comprises one or more clamping blocks 112 respectively disposed at one or more positions at the bottom 102 of the mask body 110, so that when the mask 100 is in use (i.e., being put on the face of a subject), the one or more clamping blocks 112 will be substantially disposed at positions that are below the two nostrils of the subject and to hold the removable cartridge 120 in place (i.e., in an open state). The one or more clamping blocks 112 serve the purpose of removably engaging with the removable cartridge 120. The removable cartridge 120 includes in its structure, a cartridge body 122 having a chamber 124 for housing substances exhaled from the nose of the subject; a door 126 coupled to the cartridge body 122 for removably engaging with the one or more clamping blocks 112; and a driving means 128 operably coupled to the mask body 110, the cartridge body 122, and the door 126 for opening or closing the door 126. In the case when the removable cartridge 120 is coupled to the mask body 110 by engaging the door 126 with the one or more clamping blocks 112, which results in the door 126 staying in an open state. In the case when the removable cartridge 120 is removed and no longer coupled to the mask body 110 by disengaging the door 126 from the one or more clamping blocks 112, then the door 126 is automatically closed via the driving means 128 that results in closing the chamber 124. According to embodiments of the present disclosure, the number of the clamping blocks required for operating the present sampling mask may vary with the type of door and/or driving means used in the present sampling mask. In case when the door consists of just one piece of plank, then at least one clamping block is needed for engaging the cover, and allowing the driving means to drive the door to move laterally and/or vertically to open and/or close the chamber. In case when the door consists of multiple planks (i.e., two or more planks), then at least two clamping blocks are needed for engaging the door, and allowing the driving means to drive the door to move laterally and/or vertically to open and/or close the chamber. A skilled artisan will be able to determine or choose suitable number, size, and/or type of the clamping blocks for use in the present sampling mask without undue experimentation.

When the present sampling mask 100 is in use, that is, when a subject puts the mask body 110 on his/her face and covers the nose, the removable cartridge 120 will be automatically disposed at the position right below the nose (See FIG. 1B), so that any substances exhaled from the two nostrils of the subject may be collected or harvested into the chamber 124. Preferably, the chamber 124 of the cartridge body 122 further includes a carrier for carrying the exhaled substances of the subject. In certain embodiments, the interior of the entire chamber 124 is coated with the carrier. Examples of the carrier suitable for use in the present disclosure include, but are not limited to, active carbon, alumina, carbon molecular sieve, polyacrylamide, silicone, zeolite, aminobenzyl methylcellulose, amionphenylene sulfide cellulose, diethylamine ethylcellulose, nitrobenzyl methylcellulose, nitrocellulose, and polyvinylidene fluoride.

Alternatively, or optionally, the chamber 124 is permanently or temporarily compartmented into two or more compartments for the storage of one or more agents suitable for identifying matters in the exhaled substances. In some embodiments, the two or more compartments are fluidly connected to each other, and/or to the chamber 124 itself, so that the one or more agents housed therein may freely flow from one compartment to another compartment, and/or to the chamber 124. In other embodiments, the two or more compartments are independently isolated from each other, and/or the chamber 124 itself. Thus, the one or more agents housed therein are prevented from contacting with each other. In the case when the chamber 124 is temporarily compartmentalized into one or more compartments, the compartment may be made of a degradable material, such as a thermolytic plastic. Alternatively, the compartment wall may be degraded or collapsed by light, oxidation, biodegradation, thermalization, or solvation; accordingly, the agent housed in the compartment is released into the chamber 124 upon degradation or collapse of the compartment wall. The agent housed in the one or more compartments may be quality control agents (e.g., standards of exhaled substances, negative controls, washing buffers and etc), or detecting agents (e.g., nucleic acids, chemical compounds and etc). In one embodiment, the agents housed in the one or more compartments react with the exhaled substances, so as to identify the exhaled substances. Additionally or alternatively, at least one agent housed in the compartment is a standard, which does not react with the exhaled substances, but for comparison after the other agents (i.e., agents that are not standards) had reacted with the exhaled substances.

Figure 1C:
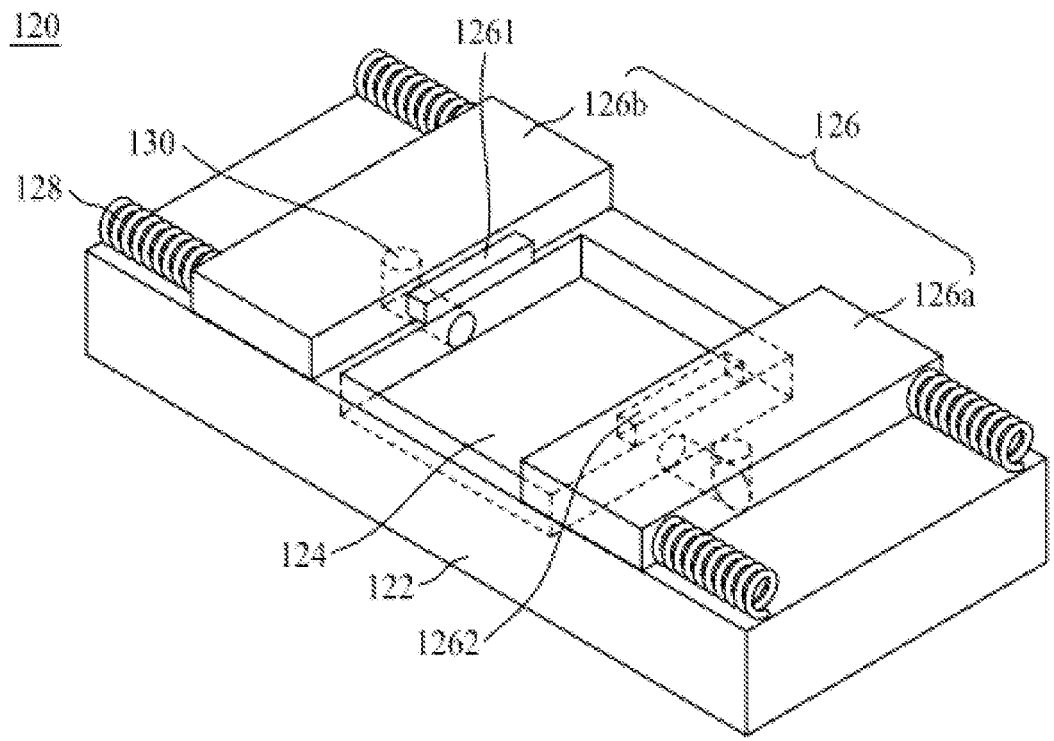
FIGS. 1C and 1D are schematic diagrams depicting the removable cartridge 120 of the sampling mask 100 with the chamber 124 being in open (FIG. 1C) and close (FIG. 1D) states, respectively.
Figure 1D:
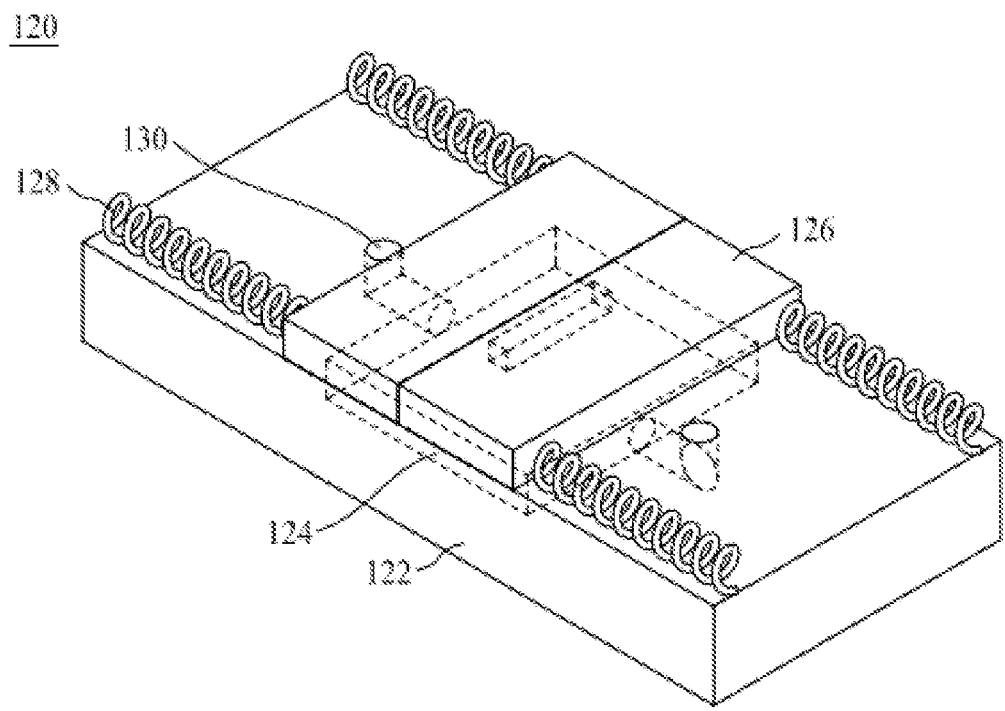

Additionally or alternatively, the cartridge body 122 may further include one or more conduits 130 independently coupling to the chamber 124 (See FIG. 1D). The conduit 130 is used to inject or remove agents (e.g., the quality control agent, and the detecting agent described above) in and/or out of the chamber 124 without opening the door 126, thereby prevent the substances housed in the chambers from contacting surrounding environment. The agents may be same or different. Additionally or alternatively, the one or more conduits 130 is/are connected to the one or more compartments of the chamber 124. For example, a first agent (e.g., a negative control, a standard and etc) may be housed in the chamber 124 prior to the use of the present sampling mask 100, then depending on the need of the use, a second agent (e.g., a detecting agent) may be introduced into the chamber through the one or more conduits 130 without opening the door 126. The exhaled substances collected in the chamber 124 may be identified by any one of assays well known in the art, such as in situ hybridization (ISH), enzyme linked immunosorbent assay (ELISA), radioimmunoassay (RIA), immunofluorescence (IFA) and the like. Thus, agents for use in any one of the assays may be injected to or removed from the chamber 124 via the conduit 130. In the case when the substances intended to be identified are microorganisms, then specific antibodies of said microorganisms may be injected into the chamber 124 through the conduits 130 to react with the microorganisms, any excess agents may also be removed from the chamber 124 through the conduits 130. Alternatively or additionally, to facilitate identification, a second reagent, such as isotopes labeled antibodies ($^{125}$I-antibodies), may also be injected into and/or removed therefrom the chamber 124 through the conduit 130.

The door 126 above the chamber 124 is sized to completely cover the chamber 124, and may be driven to move in relative to the cartridge body 122 by the driving means 128 to open or close the chamber 124. In general, the door 126 sits on rails (not visible from the drawing), which are part of the driven mechanism 128, and is pulled by springs, magnets, a rubber band, guiding members and the like, which are also part of the driving mechanism 128, to move along the rail, in relative to the cartridge body 122, thereby results in opening or closing the chamber 124.

The door 126 is made of a material that is transparent, translucent, or opaque. Examples of the material that is transparent or translucent include, but are not limited to, glass or plastics (e.g., polyethylene terephthalate (PET), high density polyethylene (HDPE), polyvinylchloride (PVC), low density polyethylene (LDPE), polypropylene (PP), polystyrene (PS), polycarbonate (PC), polylactic acid (PLA), acrylonitrile butadiene styrene (ABS), poly(methyl methacrylate) (PMMA), and a combination thereof). Examples of the material that is opaque include, but are not limited to, rigid plastics, rubbers, composite materials, and steels. Preferably, the door 126 is made of a transparent and/or translucent material, so that the entire cartridge 120 may be subjected to optical analysis without opening the door 126 to expose the contents in the chamber 124, thereby eliminating the chance of the contents being cross-contaminated by the environment or by the process dealing with handling the sampling device with hand(s) or additional tools. Alternatively, the door 126 is made of an opaque material to prevent any light-sensitive substances in the collected exhaled substances from being degraded by light.

Referring to FIGS. 1C and 1D, which depict the removable cartridge 120 in the open and close states, respectively. As shown in FIG. 1C, the cartridge 120 has a door 126 that consists of two planks 126a, 126b. Each of the two planks 126a, 126b is independently disposed on one side of the chamber 124 and coupled to the driving means 128 to move laterally with respective to the cartridge body 122. Optionally, one of the two planks 126a, 126b further includes a flange 1261, and the other plank further includes a trough 1262 for receiving the flange 1261 therein thereby tightly seals the chamber 124 when the two planks 126a, 126b are close. Referring to FIGS. 1A, 1B and 1C, in which when the sampling mask 100 is in use (i.e., being put on the face of a subject), the one or more clamping blocks 112 of the mask body 110 will hold the door 126 in place, thereby keeping the chamber 124 of the cartridge 120 in the open state (See FIGS. 1A and 1C). After sampling, the entire cartridge 120 may be removed from the mask 100, specifically, by moving the one or more clamping blocks 112 out of the way of the door 126, thereby closing the chamber 124 when the cartridge 120 is separated from the mask body 110 (See FIG. 1D).

Figure 2A:
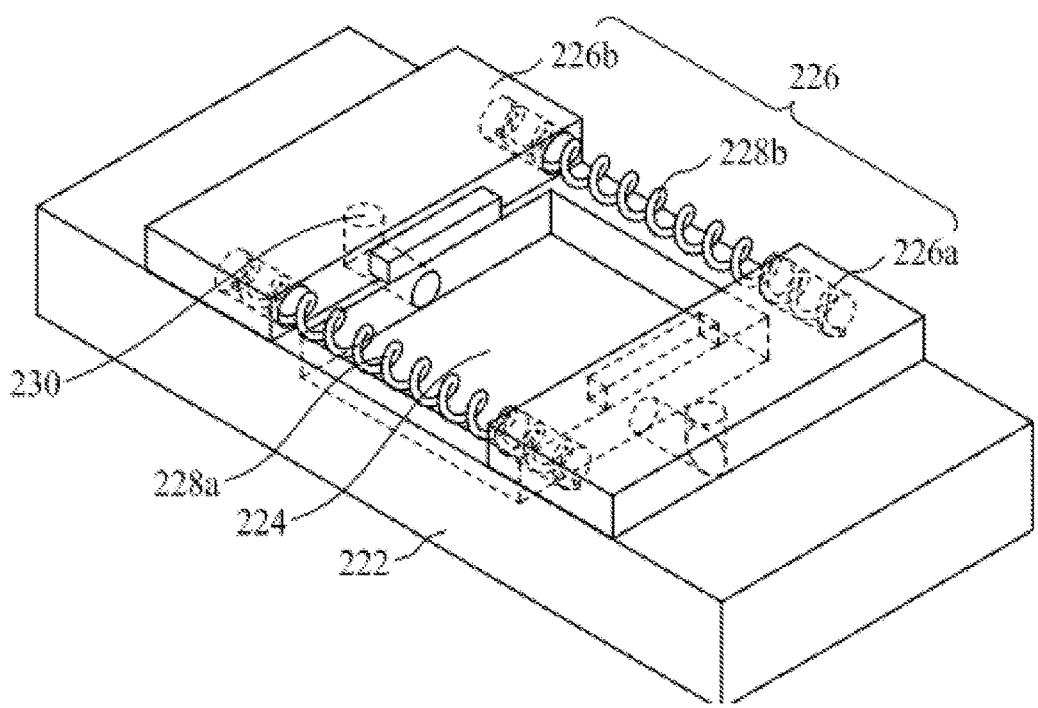
FIGS. 2A and 2B are schematic diagrams depicting the removable cartridge 220 of a sampling mask 200 with the chamber 224 being in open (FIG. 2A) and close (FIG. 2B) states, respectively.
Figure 2B:
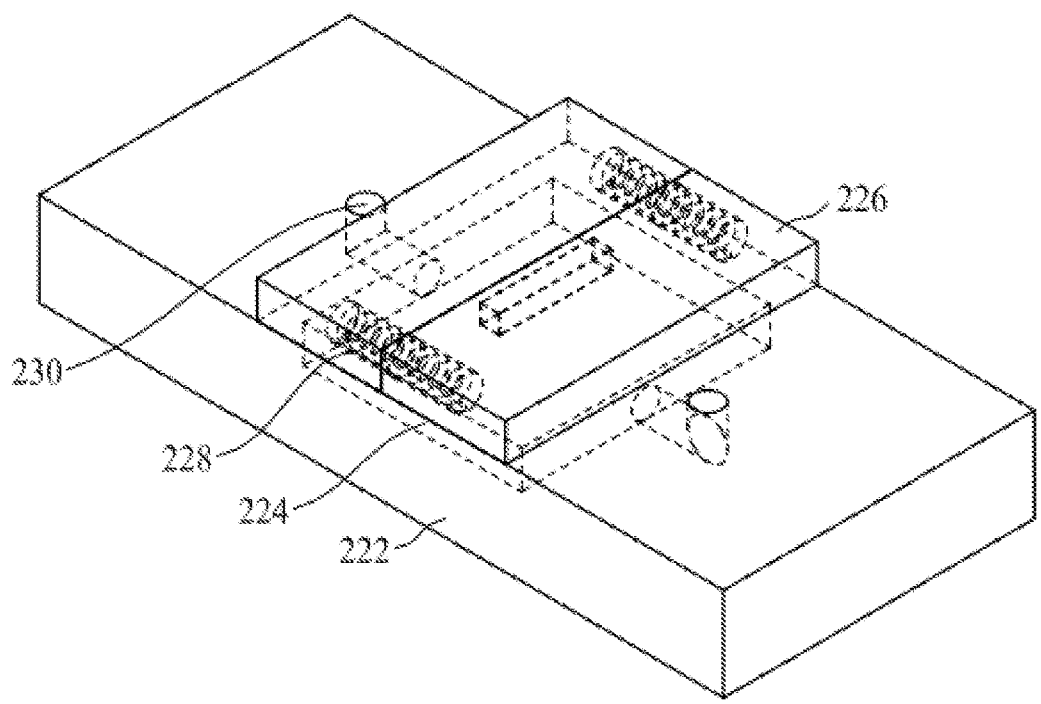

Referring to FIGS. 2A and 2B, which depict another embodiment of the present sampling mask with the cartridge 220 in the open and close states, respectively. The arrangement of components in this embodiment is relatively the same as that in FIGS. 1A to 1D except the driving means 228. The driving means 228 in this example consists of springs and rails, in which the rails are disposed underneath the door, thus are not visible from FIGS. 2A and 2B. As depicted, the two springs 228a, 228b of the driving means 228 are respectively housed in the two planks 226a, 226b of the door 226 in a way that they remained unexposed until the chamber 224 is open or when the two planks 226a, 226b are in open state, in such case, the one or more clamping blocks (e.g., the one or more clamping blocks 112) of the mask body (not depicted in FIG. 2) will hold the door 226 in place and keep the two springs 228a, 228b from closing (FIG. 2A). Once the one or more clamping blocks are moved out of the way, the two planks 226a, 226b will spring close (FIG. 2B) thereby closing the chamber 224 and allowing the entire cartridge 220 to be taken out or separated from the mask body (not depicted) for further analysis (e.g., identifying the species in the exhaled substances collected in the chamber 224).

Figure 3A:
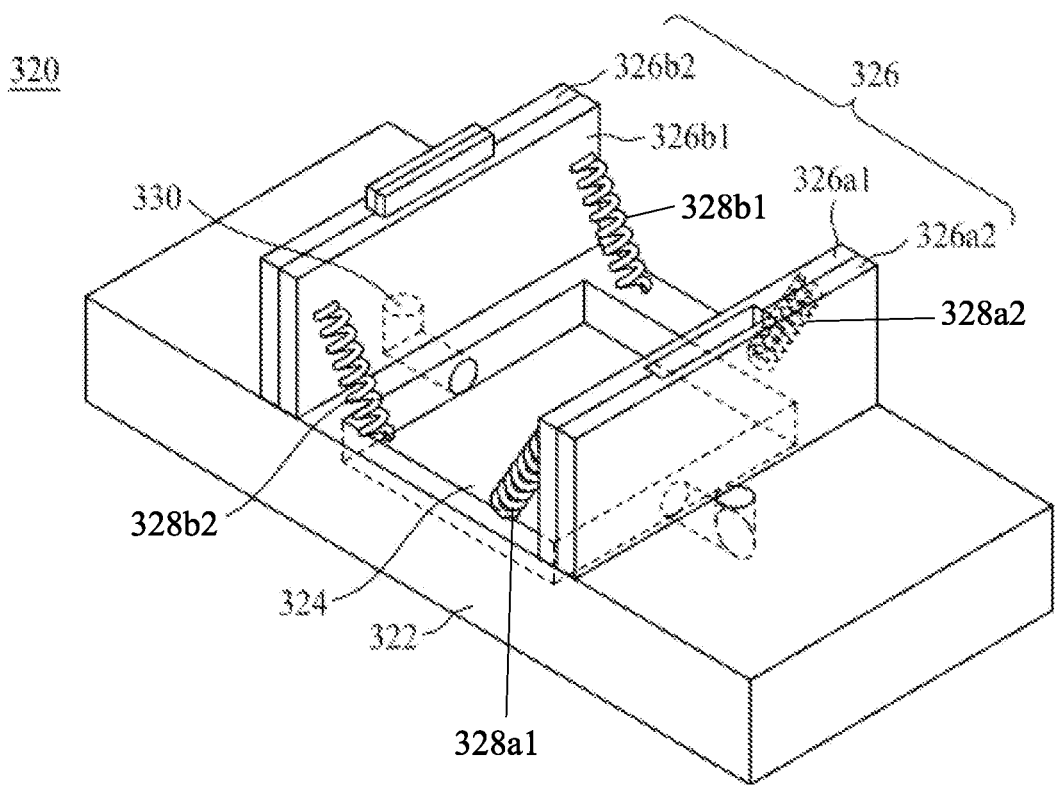
FIGS. 3A and 3B are schematic diagrams depicting the removable cartridge 320 of the sampling mask 300 with the chamber 324 being in open (FIG. 3A) and close (FIG. 3B) states, respectively.
Figure 3B:
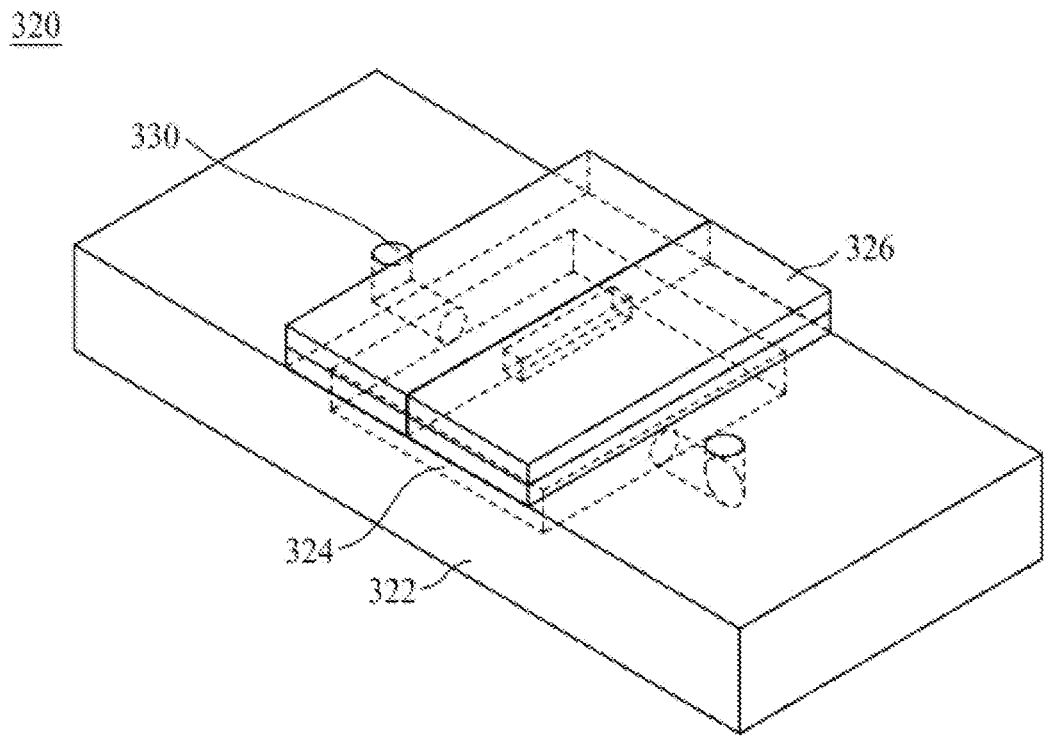

FIGS. 3A and 3B depict another embodiment of the sampling mask with the cartridge 320 respectively in the open and close states. The arrangement of components in this embodiment is relatively the same as that in FIG. 2 except the door 326 and the driving means 328. In this embodiment, the door 326 is the so called "double-plank type" of door. Instead of having one plank on each side of the door as depicted in FIG. 2, each side of the door is composed of two pieces of planks (e.g., the planks $326a_1$ and 326$a_2$, or planks 326$b_1$ and 326$b_2$) hinged together, with one of the two pieces (e.g., the planks 326$a_2$, and 326$b_2$) being fixed to one side of the chamber 324, while the other piece (e.g., the planks 326$a_1$ or 326$b_1$) is coupled to the driving means 328 on the non-hinged side. Note that the hinge is not visible from the drawing. The driving means 328 in this embodiment includes at least four springs (328$a_1$, 328$a_2$, 328$b_1$, 328$b_2$), with two springs (e.g., the springs 328$a_1$, 328$a_2$) being independently connected to one piece of the plank (e.g., the plank 326$a$1) at one end and to the cartridge body 322 at the other end so that the two springs (e.g., the springs 328$a_1$, 328$a_2$) may drive the plank (e.g., the plank 326$a$1) to move vertically (i.e., upwardly or downwardly) resulted in opening or closing the chamber 324. In the open state, the one or more clamping blocks (e.g., the one or more clamping blocks 112) of the mask body (not depicted in FIG. 3) will hold the door 326 in place and keep the driving means 328 from closing the door 326 (FIG. 3A). Once the one or more clamping blocks are moved out of the way, the two planks 326$a$, 326$b$ will spring close (FIG. 3B), allowing the entire cartridge 320 to be taken out or separated from the mask body (not depicted) for further analysis (e.g., identifying the species in the exhaled substances collected in the chamber 324).

Figure 4A:
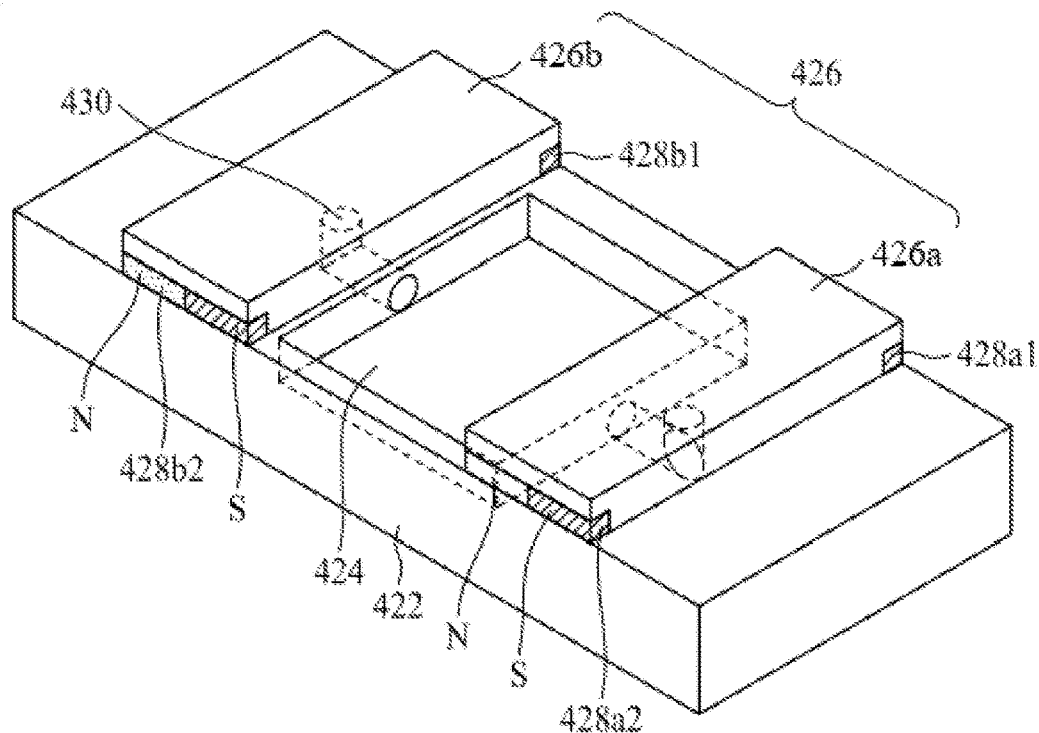
FIGS. 4A and 4B are schematic diagrams depicting the removable cartridge 420 of the sampling mask 400 with the chamber 424 being in open (FIG. 4A) and close (FIG. 4B) states, respectively.
Figure 4B:
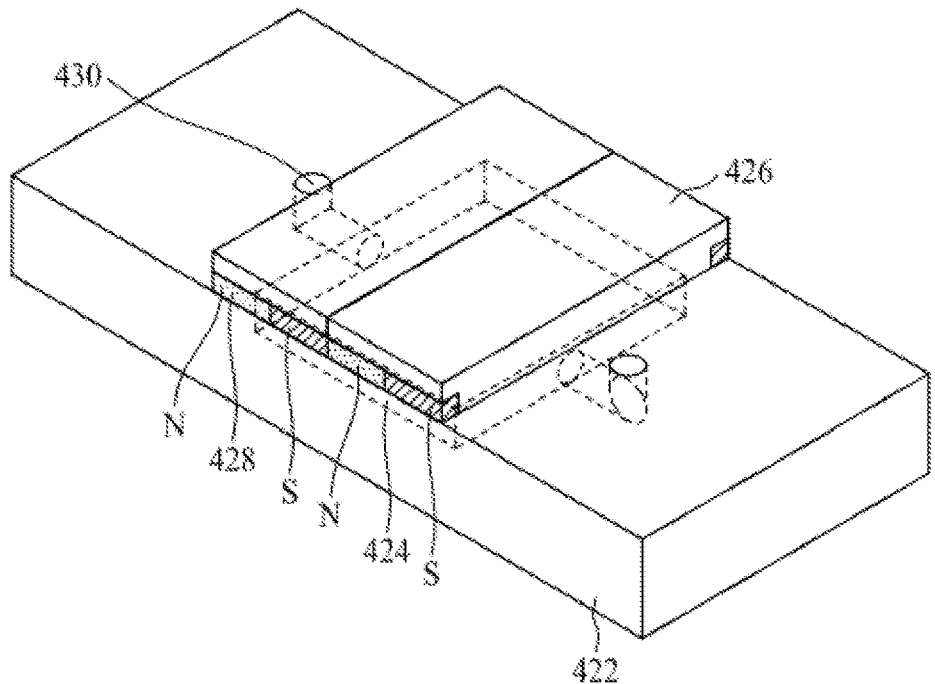

FIGS. 4A and 4B depict another embodiment of the sampling mask-41W with the cartridge 420 respectively in the open and close states. The arrangement of components in this embodiment is relatively same as that in FIG. 2 except the driving means 428. Different from embodiments depicted in FIGS. 1 to 3, in this embodiment, two sets of magnets are used to replace the springs and/or a combination of a rail and sliding blocks. Each set of magnets consists of two magnets respectively embedded in the upper and lower ends of the back side (i.e., the side of a plank that faces the chamber) of a plank. Specifically, two magnets 428$a_1$, 428$a_2$ are respectively embedded in the upper and lower ends of the back side of plank 426$a$ with their respective north poles facing toward the other plank, i.e., plank 426$b$. Similarly, the other two magnets 428$b_1$, 428$b_2$ are respectively embedded in the upper and lower ends of the back side of the plank 426$b$ with their respective south poles facing toward the plank 426$a$. By this arrangement, the two planks 426$a$, 426$b$ will automatically close due to the attraction between the north and south poles of the two sets of magnets (FIG. 4B).

Figure 5A:
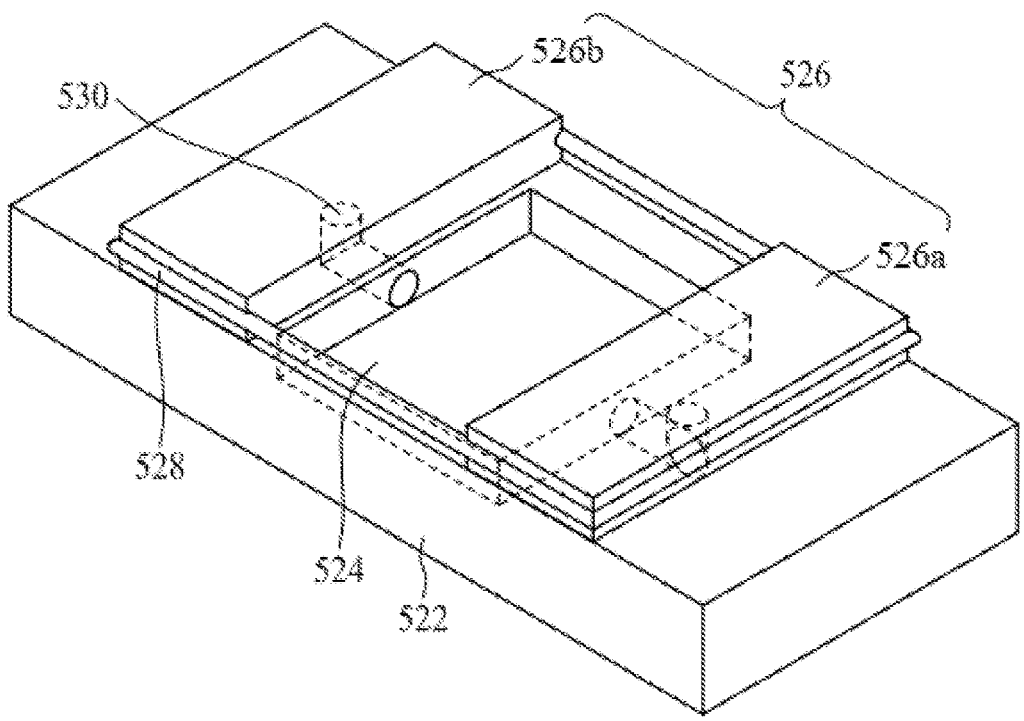
FIGS. 5A and 5B are schematic diagrams depicting the removable cartridge 520 of the sampling mask 500 with the chamber 524 being in open (FIG. 5A) and close (FIG. 5B) states, respectively.
Figure 5B:
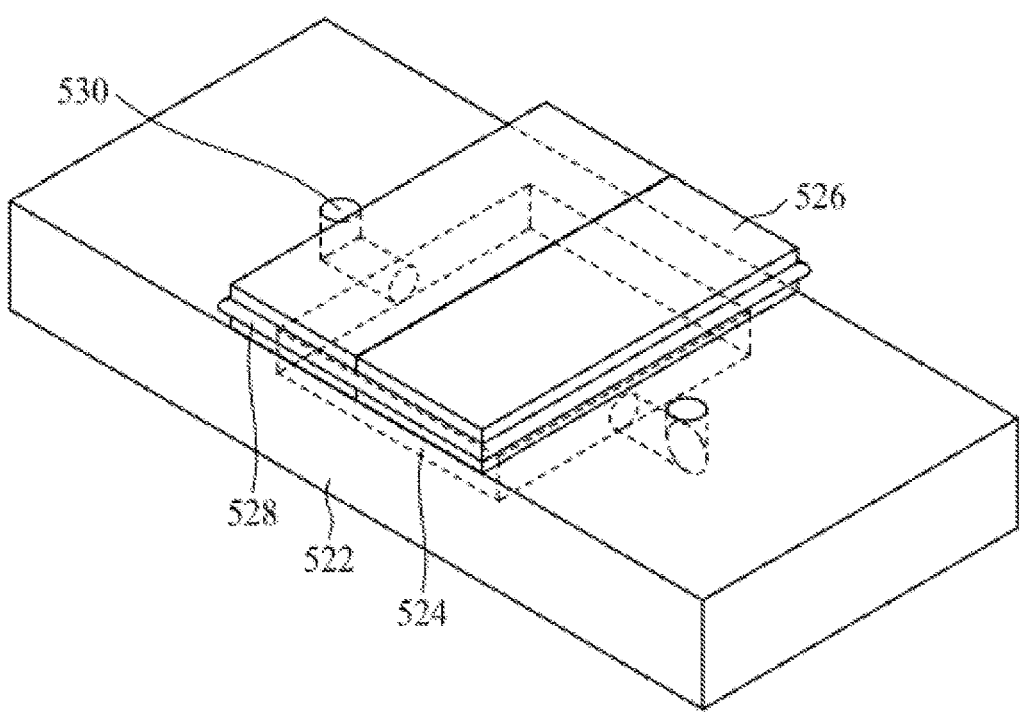

FIGS. 5A and 5B depict another embodiment of the sampling mask with the cartridge 520 respectively in the open and close states. The arrangement of components in this embodiment is relatively same as that in FIGS. 1 to 2 except the driving means 528. In this embodiment, an elastic rubber band serves as the driving means 528 and wraps around the outer perimeter of the two planks 526$a$, 526$b$. To open the chamber 524, the elastic rubber band 528 is stretched to allow the one or more clamping blocks (not depicted) to hold the chamber 524 in the open state (FIG. 5A). By contrast, once the one or more clamping blocks (not depicted) is/are moved out of the way, the elastic rubber band 528 will spring back automatically to close the door 526, accordingly, the chamber 524 (FIG. 5B).

Figure 6A:
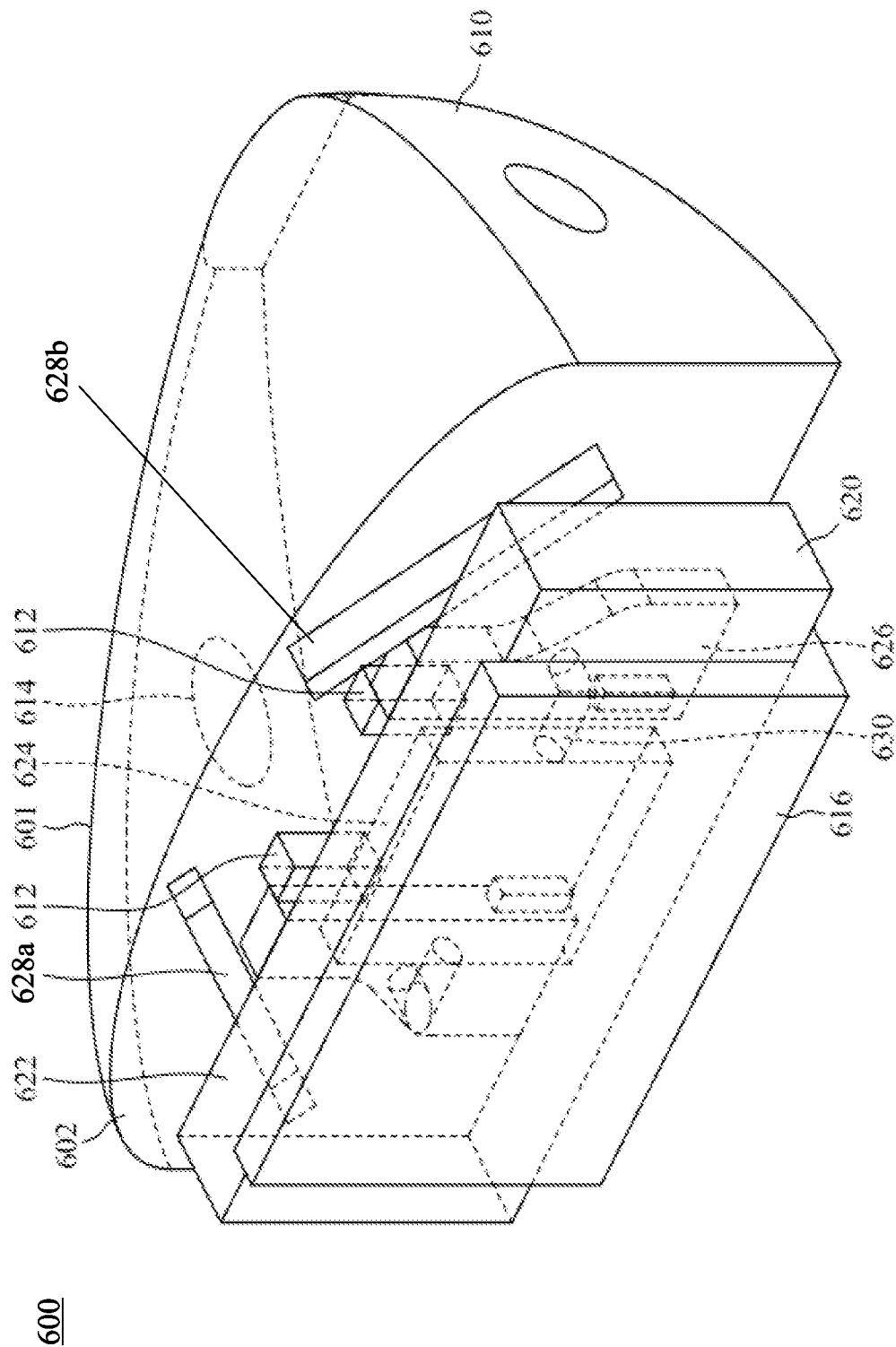
FIG. 6A is the bottom view of a sampling face mask 600 in accordance with one embodiment of the present disclosure.
Figure 6B:
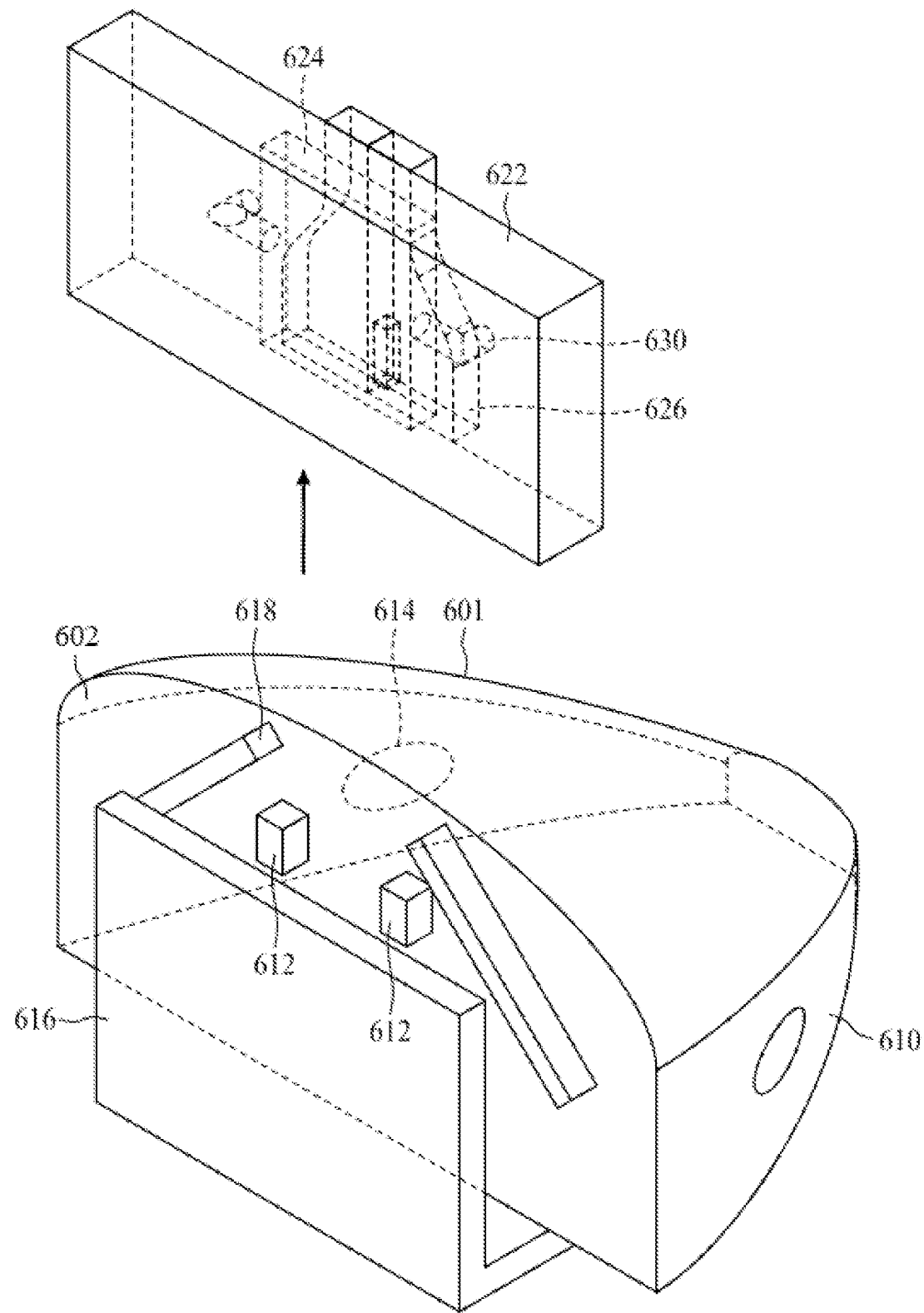
FIG. 6B is the bottom view depicting the removable cartridge 620 being taken out of the sampling face mask 600 of FIG. 6A.

FIG. 6 depicts another embodiment of the present sampling mask 600, with the removable cartridge 620 being coupled to the mask body 610 (FIG. 6A) or disengaged therefrom (FIG. 6B). The arrangement of components in this embodiment is relatively same as that in FIG. 1 except the driving means 628, which includes two guiding members 628$a$, 628$b$ respectively disposed not on the cartridge body 620 as that in FIG. 1, but on the side of the bottom 602 that faces the removable base 612 of the mask body 610. When the sampling mask 600 is put on the face of a subject, the removable cartridge 620 is placed on the base 616 with the door 626 being held in the open state via the one or more clamping blocks 612, thus keeping the chamber 624 open. After sampling, the removable cartridge 620 may be sliding out of the base 616 to separate from the mask body 610, and the door 626 of the chamber 624 is closed via the two guiding members 628$a$, 628$b$ while sliding out (FIG. 6B). The entire cartridge 620 may then be subjected to further analysis for the identification of substances collected therein.

Figure 7A:
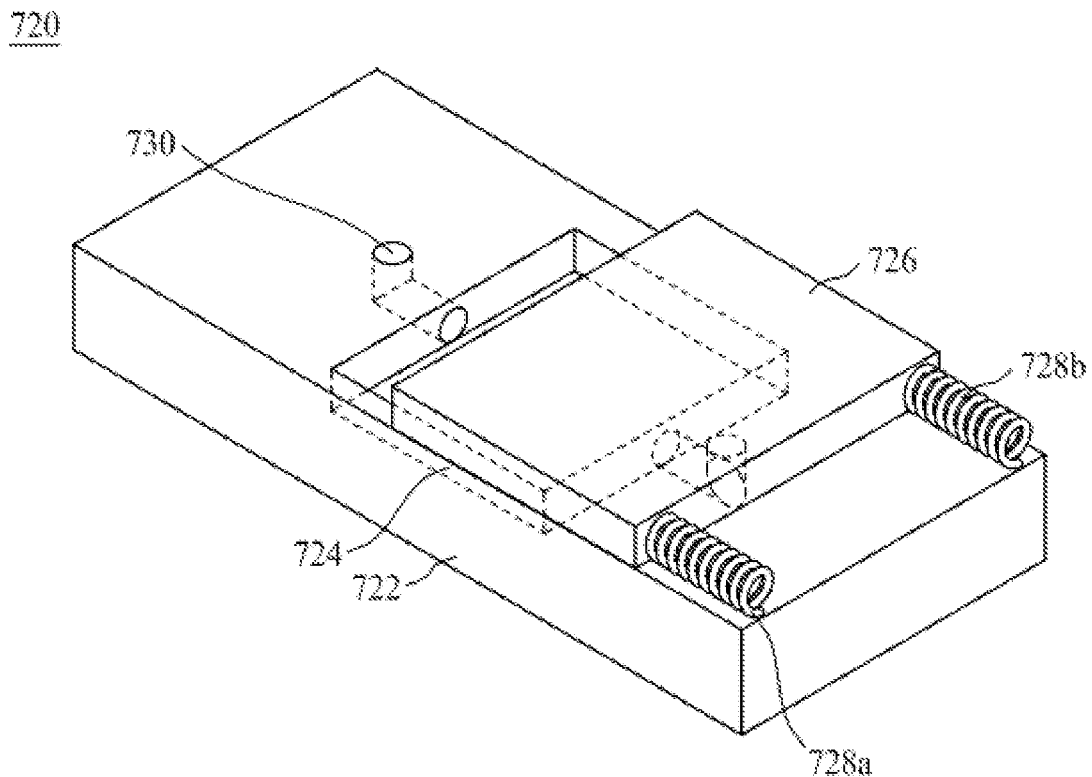
FIGS. 7A and 7B are schematic diagrams depicting the removable cartridge 720 of the sampling mask 700 with the chamber 724 being in open (FIG. 7A) and close (FIG. 7B) states, respectively.
Figure 7B:
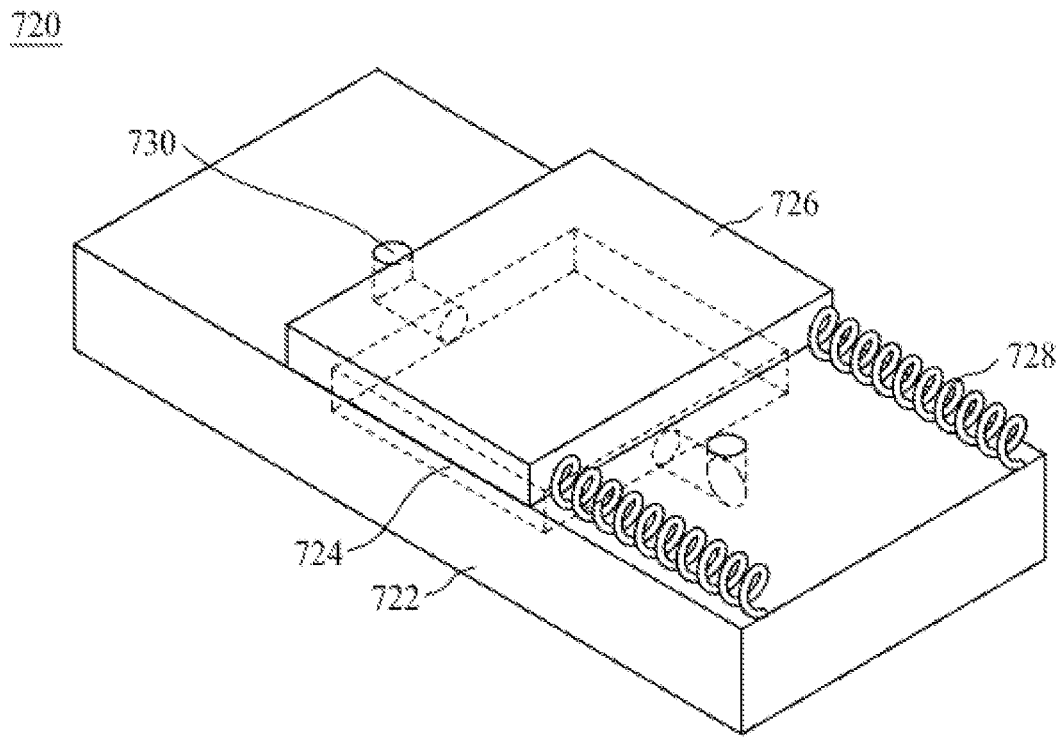

FIGS. 7A and 7B depict another embodiment of the present sampling mask with the cartridge 720 respectively in the open and close states. The arrangement of components in this embodiment is relatively same as that in FIG. 1 except the door 726 consists of a single plank. Like the configuration in FIG. 1, the door 726 sits on rails (not visible from the drawings) and is driven to move laterally along the cartridge body 720 via the driving means 728 (i.e., the two springs 728$a$, 728$b$), thus results in opening or closing the chamber 724. To open the chamber 724, the two springs 728$a$, 728$b$ are stretched to allow the one or more clamping blocks (not depicted) to hold the chamber 724 in the open state (FIG. 7A). By contrast, once the one or more clamping blocks is/are moved out of the way, the two springs 728$a$, 728$b$ will spring back automatically to close the door 726, accordingly, the chamber 724 (FIG. 7B).

Figure 8A:
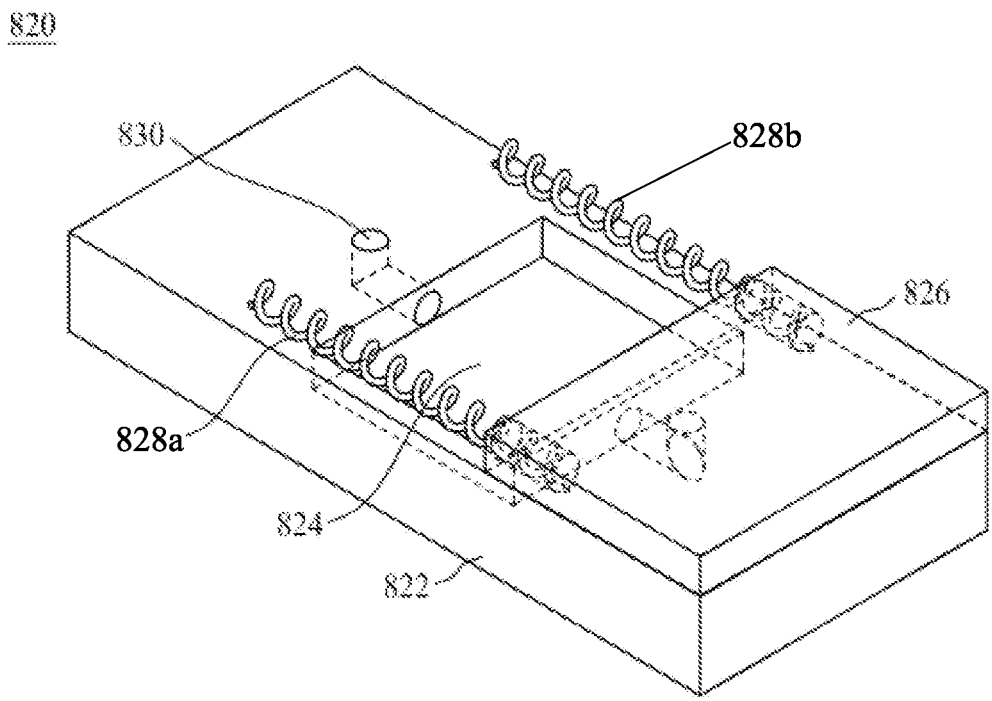
FIGS. 8A and 8B are schematic diagrams depicting the removable cartridge 820 of the sampling mask 800 with the chamber 824 being in open (FIG. 8A) and close (FIG. 8B) states, respectively.
Figure 8B:
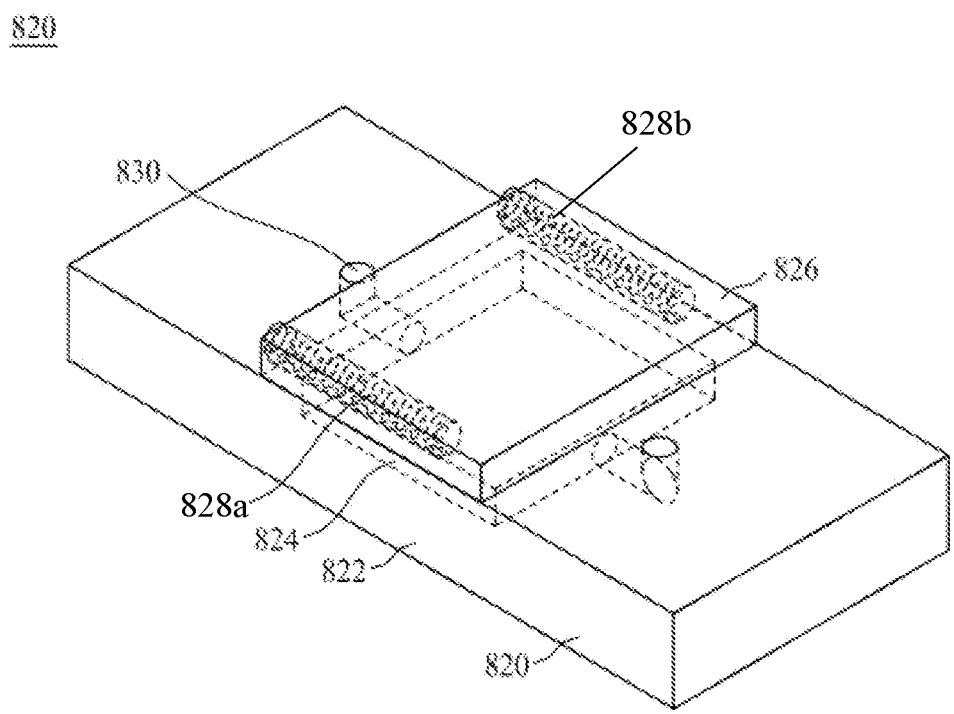

FIGS. 8A and 8B depict another embodiment of the present sampling mask with the cartridge 820 respectively in the open and close states. The arrangement of components in this embodiment is relatively same as that in FIG. 7 except the driving means 828. As depicted, instead of being disposed at the corners of the cartridge body 820, the two springs 828$a$, 828$b$ are received in the door 826 when the chamber 824 is close, and are revealed when the chamber 824 is kept in open state by the one or more clamping blocks (not depicted in the drawing).

Taken together, the present sampling mask addresses the contamination issue of existing sampling technique by providing an improved cartridge that is automatically closed and taken out for subsequent analysis once the sampling is completed.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A sampling face mask for collecting substances exhaled from the nose of a subject, comprising:
   a mask body having a front side conforming to the shape of the nose of the subject, a bottom, and one or more clamping blocks disposed on the bottom;
   a removable cartridge removably coupled to the mask body comprising:
   a cartridge body having a chamber for housing the substances exhaled from the nose of the subject; and
   a door disposed above the chamber for opening or closing the chamber, and a driving means operably coupled to the mask body, the cartridge body, and the door for driving the door to move laterally or vertically with respect to the cartridge body thereby opening or closing the chamber;

wherein, the one or more clamping blocks of the mask body can hold the door in place thereby keeping the door from closing and the chamber being disposed underneath the nose and stayed open; and when the one or more clamping blocks does not hold the door in place, the door is driven closed via the driving means thereby closing the chamber, and allowing the removable cartridge to be separated from the mask body.

2. The sampling face mask of claim 1, wherein the mask body has one or more breathable areas respectively disposed at positions corresponding to both sides of the nose.

3. The sampling face mask of claim 1, further comprising a base coupled to the bottom of the mask body for receiving the removable cartridge thereon.

4. The sampling face mask of claim 1, wherein the driving means is a spring, a magnet, a rubber band, a rail, a guiding member, or a combination thereof.

5. The sampling face mask of claim 1, wherein the chamber is compartmented into one or more compartments.

6. The sampling face mask of claim 5, wherein the cartridge body further comprises one or more conduits independently coupled to the one or more compartments.

7. The sampling face mask of claim 1, wherein the door consists of one or more pieces of planks, and is driven to move laterally or vertically with respect to the cartridge body via the driving means.

8. The sampling face mask of claim 7, wherein the door is made of transparent, translucent, or opaque material.

9. The sampling face mask of claim 1, wherein the chamber is filled with or coated with a carrier for carrying the exhaled substances.

10. The sampling face mask of claim 9, wherein the carrier is selected from the group consisting of active carbon, alumina, carbon molecular sieve, polyacrylamide, silicone, zeolite, aminobenzyl methylcellulose, aminophenylene sulfide cellulose, diethylamine ethylcellulose, nitrobenzyl methylcellulose, nitrocellulose, and polyvinylidene fluoride.

* * * * *